United States Patent [19]

Byrne

[11] Patent Number: 4,697,025

[45] Date of Patent: Sep. 29, 1987

[54] CARBOXYLATE SALT COMPOUND AND METHOD FOR FLAVORING FOODSTUFFS AND TOBACCO

[75] Inventor: Brian Byrne, Mahwah, N.J.

[73] Assignee: Hercules Incorporated, Wilmington, Del.

[21] Appl. No.: 776,300

[22] Filed: Sep. 16, 1985

[51] Int. Cl.⁴ .............................................. C07F 5/06
[52] U.S. Cl. ................................... 556/183; 562/587; 426/533; 426/599
[58] Field of Search ......................... 556/183; 562/587

[56] References Cited

PUBLICATIONS

Chemical Abstracts 102 167060f (1984).
Tetrahedron Letters, vol. 25(47), pp. 5409-5412.
Oser et al, Food Technol 39(11), pp. 108-117 (1985).

Primary Examiner—Helen M. S. Sneed
Attorney, Agent, or Firm—Dale R. Lovercheck

[57] ABSTRACT

Carboxylates having the general formula:

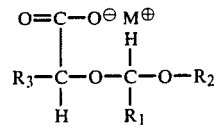

and a method of flavoring foodstuff and tobacco compositions therewith wherein $R_1$ is an alkyl having from 1 to 14 carbons, alkenyl having from 2 to 14 carbons, cycloalkyl, cycloalkenyl, aryl, or furyl having from 4 to 14 carbons; $R_2$ is alkyl, alkenyl, alkynyl, cycloalkyl, cycloalkenyl, or cycloalkynyl of from 1 to 7 carbons, aryl or oxyaryl of from 5 to 18 carbons, or a cycloaliphatic ether of from 5 to 6 carbons; and $R_3$ is hydrogen, alkyl, alkenyl, alkynyl, cycloalkyl, cycloalkenyl, or cycloalkynyl of from 1 to 7 carbons, aryl, or oxyaryl of from 5 to 18 carbons, or a cycloaliphatic ether of from 5 to 6 carbons, or a radical of the general formula:

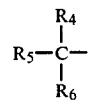

where $R_4$ and $R_5$ independently are hydrogen or alkyl of from 1 to 6 carbons; and $R_6$ is aryl, alkylaryl, aryloxy, alkoxy, cyclic acetal of from 3 to 7 carbons, dioxyalkyenyl ether of from 4 to 8 carbons; and M is cation other than hydrogen ion.

11 Claims, No Drawings

CARBOXYLATE SALT COMPOUND AND METHOD FOR FLAVORING FOODSTUFFS AND TOBACCO

This invention relates to a novel neutralized carboxylate. The carboxylates act as aldehyde generators by responding to the conditions of use of a food product in which the carboxylates are incorporated to yield generated aldehydes. This invention also relates to use of carboxylate salts in flavors to generate the desired aldehydes.

It is well known that both acetaldehyde and propionaldehyde occur in a wide variety of fresh and prepared foodstuffs, such as fruits, meat, dairy products, baked goods and vegetables. Acetaldehyde has been found particularly important in contributing to the flavor impact and "fresh" effect of certain foodstuffs, especially of the citrus fruit and red berry types. As such, it is indispensable in compounding artificial flavors where the "fresh effect" is needed. The same can be said of propionaldehyde, which also contributes to the flavor of a wide range of fruit and food types.

Other aliphatic aldehydes, such as butyraldehyde, octylaldehyde, and the like, varying in carbon number from $C_4$ to about $C_{12}$, are known for giving impact and special flavor effects in a wide variety of flavors corresponding to their occurrence in nature in a wide variety of foodstuffs and these other aldehydes can also be fixed according to the principles of this invention.

Much effort has been expended in the last two decades, as attested by patent literature on the subject, to provide a stable "fixed" form of acetaldehyde which would release only under the desired conditions of use and not before. Boden, in U.S. Pat. No. 4,296,138, disclosed fixing acetaldehyde by formation of acetate. However, these acetates hydrolyze readily in ambient humidity, and consequently are difficult to form and store in food compositions. The main difficulty in "fixing" acetaldehyde lies in its physical characteristics of being a gas at room temperature (21° C.) Under normal ambient conditions, being miscible with water, and having a high degree of chemical reactivity and instability. Its chemical instability is exemplified by its tendency to polymerize or form paraldehyde and metaldehyde, oxidize to acetic acid, or combine chemically with itself and other materials in the presence of an acid or base.

To accomplish fixation of acetaldehyde, workers have tried chemical derivatization. Chemical derivatization must satisfy several, often conflicting requirements, including that of chemical inertness and stability under the usual storage conditions. For example, were the acetal to contain an acid functionality, the acetal will undergo autohydrolysis and that the aldehyde would be liberated before it could be fixed in the foodstuff containing such an acetal. Another requirement is the quick release of aldehyde upon mixing or preparing the food product for use. And in many foodstuffs, such as dry beverage mixes, it is a requirement that the quick release occur at temperatures as low as about 10° C. yet another requirement is that the acetal and the residue produced upon hydrolysis not interfere with the aroma or taste of the desired flavor. To satisfy this requirement, the derivative and its conversion products, other than the target aldehyde, should be relatively odorless and tasteless. For example, it is generally undesirable to have the acetal and the residue contain ester functionalities because esters might interfere with the desired taste. An additional requirement is that the residue have good solubility in water.

Many attempts to provide suitable chemical derivatives for generating acetaldehyde are evinced in the patent literature. A variety of aldehyde derivatives have been proposed for generating acetaldehyde, including carbamates, carbonates, ureas, ethylidene compounds (U.S. Pat. No. 2,305,620) and certain carboxylates (U.S. Pat. Nos. 3,829,504 and 3,857,964). All the aforementioned derivatives suffer from at least some of the disadvantages of producing off-tastes, being toxic, or being too unreactive to release at an appropriate rate at an appropriate temperature in the desired foodstuff or in having their own taste and odor effect.

Use of well-known acetals of acetaldehyde, propionaldehyde, and other aliphatic aldehydes, up to about dodecylaldehyde, derived from monohydric alcohols, such as dimethyl, diethyl and dihexyl acetals, is precluded by the taste of the acetal itself, which is usually unacceptably different from that of the parent aldehyde, and thus interferes with the balance of the desired flavor, especially in the case of the acetals of the $C_1$ to about $C_8$ aldehydes. Moreover, use of alcohols to make such acetals is limited to those aliphatic alcohols having 1 to 5 carbon atoms, cyclohexanol or benzyl, since aliphatic alcohols of $C_6$ and higher, up to about $C_{12}$, lend their own flavor and also distort the intended flavor.

Benefits of the carboxylate compounds of the invention are their stability; "fixation" of aldehydes in flavors and flavored food bases; and provision of a quick release of aldehydes under the conditions of intended use, such as being in liquid at or above 10° C. The carboxylates of the invention also do not interfere with the desired flavor, are stable to moisture, heat, and oxidation under normal conditions of storage, are capable of being incorporated into a dry flavor and remaining stable, and provide a higher percentage of stable, fixed carboxylatedehyde in a dry flavor or flavor base than has heretofore been found possible.

The compound of the invention has the general formula:

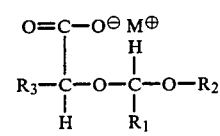

I where R is an alkyl having from 1 to 14 carbons, alkenyl having from 2 to 14 carbons, cycloalkyl, cycloalkenyl, aryl, or furyl having from 4 to 14 carbons; $R_2$ is alkyl, alkenyl, alkynyl, cycloalkyl, cycloalkenyl, or cycloalkynyl of from 1 to 7 carbons, aryl or oxyaryl of from 5 to 18 carbons, or a cycloaliphatic ether of from 5 to 6 carbons; and $R_3$ is hydrogen, alkyl, alkenyl, alkynyl, cycloalkyl, cycloalkenyl, or cycloalkynyl of from 1 to 7 carbons, aryl, or oxyaryl of from 5 to 18 carbons, or a cycloaliphatic ether of from 5 to 6 carbons, or a radical of the general formula:

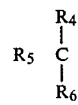

where $R_4$ and $R_5$ independently are hydrogen or alkyl of from 1 to 6 carbons; and $R_6$ is aryl, alkylaryl, aryloxy, alkoxy, cylic acetal of from 3 to 7 carbons, dioxyalkyenyl ether of from 4 to 8 carbons; and M is cation other than hydrogen ion.

The compounds of the general formula I may be made by first reacting a compound of the general formula II

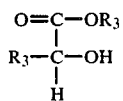

with a compound of the general formula III

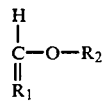

in acid to form a compound of the general formula IV

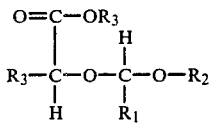

then the compound of the general formula IV is reacted with base in water and alcohol to form a compound of the general formula I.

Preferably, in the neutralized carboxylate of the general formula I, $R_1$, the aldehyde residue, is a radical selected from the group consisting of:

(a) 1 to 14 carbon hydrocarbon radicals which can be branched or straight chain alkyl or alkenyl; cycloalkyl or cycloalkenyl; aryl or benzyl; and
(b) furyl;
  (i) an aliphatic or cycloaliphatic hydrocarbon moiety of up to 7 carbon atoms corresponding to an alcohol which does not, itself, have a strong taste or odor, such as, benzyl, methyl, ethyl, propyl, t-butyl, propenyl or butenyl, but preferably, methyl or ethyl, or a benzyl group;
  (ii) a $C_2$ to $C_{18}$ aliphatic, cycloaliphatic or monocyclic aromatic acyl group or an oxygenated derivative thereof which, upon hydrolysis of the acetal linkage, yields an acid which will not distort the desired flavor; or
  (iii) a 5 or 6 carbon cycloaliphatic ether; and $R_3$ is
  (i) hydrogen;
  (ii) a hydrocarbon radical corresponding to $R_2$ with the further limitation that the total carbon number of $R_2$ and $R_3$ combined is between 9 and 14; or
  (iii) a radical of the general formula:

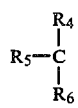

$R_4$ and $R_5$ are hydrogen or the same or different alkyl groups, and $R_6$ is a functional group selected from the class consisting of phenyl, alkyl aromatic, phenoxy, alkoxy, dioxolane, or metadioxane groups, or a hydrocarbon moiety containing such a group, consistent with the formation of a parent compound which itself has a low taste and odor, and which yields only hydrolysis products having low or compatible taste and odor; and where M is a consumable cation, such as $Na^+$, $K^+$, $Ca^{2+}$, $Al^{3+}$, $NH_4^+$ and the like.

For example, a carboxylate of Formula (I) can be synthesized by reaction of the appropriate vinyl alkyl ether with the desired betahydroxy ester in the presence of an acid catalyst as exemplified by the reaction of ethyl lactate (II) with propenyl ethyl ether (III) to form Compound IV structure followed by treatment with an alkaline metal hydroxide, such as KOH to product potassium 2-[(1'-ethoxy)propoxy]propanoate (V)

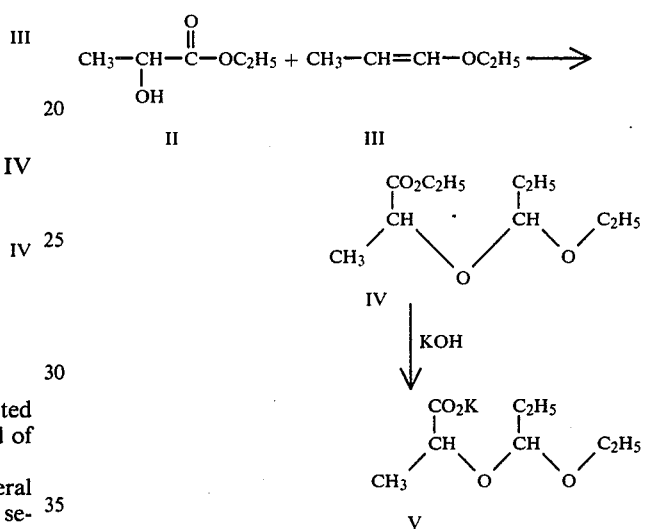

The alpha hydroxy esters found useful include ethyl lactate and diethyltartarate or any other ester of a relatively bland alpha hydroxy acid capable of forming a linear carboxylate through reaction with a vinyl ether. The molecular weight of the alpha hydroxy ester has a practical limit in the weight of the parent carboxylate derivative relative to the amount of aldehyde which can be released.

Typical vinyl ethers which can be employed include ethyl vinyl ether, ethyl propenyl ether, benzyl vinyl ether, cyclohexyl vinyl ether, ethyl butenyl ether, butyl vinyl ether, ethyl hexenyl ether, methyl octenyl ether, and methyl decenyl ether, for example.

The flavorful aldehyde is released from the carboxylate compounds of Formula (I) by the addition of water. The flavorful aldehydes are believed to be formed, for example, as follows:

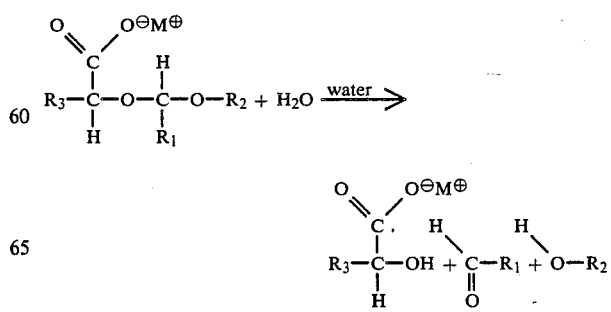

Preferably, the invention is used as a method of releasing flavorful aldehydes from foodstuffs and tobacco containing carboxylates including providing a compound of the general formula:

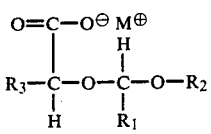

where $R_1$ is an alkyl having from 1 to 14 carbons, alkenyl having from 2 to 14 carbons, cycloalkyl, cycloalkenyl, aryl, or furyl having from 4 to 14 carbons; $R_2$ is alkyl, alkenyl, alkynyl, cycloalkyl, cycloalkenyl, or cycloalkynyl of from 1 to 7 carbons, aryl or oxyaryl of from 5 to 18 carbons, or a cycloaliphatic ether of from 5 to 6 carbons; and $R_3$ is hydrogen, alkyl, alkenyl, alkynyl, cycloalkyl, cycloalkenyl, or cycloalkynyl of from 1 to 7 carbons, aryl, or oxyaryl of from 5 to 18 carbons, or a cycloaliphatic ether of from 5 to 6 carbons, or a radical of the general formula:

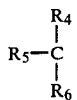

where $R_4$ and $R_5$ independently are hydrogen or alkyl of from 1 to 6 carbons; and $R_6$ is aryl, alkylaryl, aryloxy, alkoxy, cyclic acetal of from 3 to 7 carbons, dioxyalkenyl ether of from 4 to 8 carbons; and M is cation other than hydrogen ion; and adding a liquid comprising water to the mixture to form an aqueous mixture.

EXAMPLE 1

Potassium 2-[(1'-ethoxy(ethoxy]propanoate

To a 3000 mL flask containing 766 g (6.49 moles) ethyl lactate and 1.9 g 36% hydrochloric acid at 5° C. is added 700.0 g (9.72 moles) ethyl vinyl ether over a 4-hour period. After stirring one hour, the reaction is quenched with 75 g 2% sodium carbonate solution. The organic material is fractionated and 1064.4 g (86.3%) ethyl 2-[(1'-ethoxy)ethoxy]propanoate is recovered (b.p. 89°–90° C. at 17 mmHg).

To a 250 mL flask containing 38.0 g (0.20 moles) ethyl 2-[(1'-ethoxy)ethoxy]propanoate at 23° C. is added a solution of 14.8 g (0.264 moles) KOH, 30.0 g (1.667 moles) water and 10.0 g (0.217 moles) ethanol over a 30 minute period. Maintaining ±23° C., the solution is stirred for one hour, then extracted with 20 g hexane. The aqueous phase is then stripped of all solvent under vacuum. A constant weight of 43.7 g potassium 2-[(1'-ethoxy(ethoxy]propanoate is obtained as a yellowish viscous liquid.

EXAMPLE 2

Potassium 2-[(1'-ethoxy)propoxy]propanoate

To a 250 mL flask containing 37.0 g (0.31 mole) ethyl lactate and four drops 32% hydrochloric acid at 30° C. is added 71 g (0.82 mole) ethyl propenyl ether. The mixture is heated to 75° C. for thirty minutes, cooled to 25° C., then quenched with 100 g 5% sodium bicarbonate solution. The organic material was flash distilled yielding 52.3 g (90%) ethyl 2-[(1'-ethoxy)propoxy]propanoate.

To a 250 mL flask containing 52.3 g (0.27 mole) ethyl 2-[(1'-ethoxy)propoxy]propanoate at 25° C. is added a mixture of 18.5 g (0.33 mole) potassium hydroxide and 56 g (1.75 moles) methanol. After two hours at 25° C., the reaction mixture is evacuated and a very viscous liquid, 70.8 g, potassium 2-[(1'-ethoxy)propoxy]propanoate is recovered.

EXAMPLE 3

Calcium 2-[(1'-ethoxy)ethoxy]propanoate

To a 50 mL flask containing 5.9 g (0.05 mole) product of Example 1 and 6.5 g (0.36 mole) water at 20° C. is added 20 g 50% calcium chloride aqueous solution. A white crystalline solid material was isolated by filtration and dried yielding 3.6 g (20%) calcium 2-[(1'-ethoxy)ethoxy]propanoate.

EXAMPLE 4

Hydrolysis Rate of Potassium 2-[(1'-ethoxy)ethoxy]propanoate

An aqueous solution containing the product from Example 1 is adjusted to pH 3.0 with acid. The rate at which aldehyde is released can be monitored either by GLC or by U.V. (275 nm). The release rates are shown in the table below.

| Potassium 2-[(1'-ethoxy)ethoxy]propanoate (pH 3) | | | | | |
|---|---|---|---|---|---|
| TIME | % ACETALDEHYDE GENERATED | | | | |
| (MINUTES) | 5° C. | 10° C. | 15° C. | 20° C. | 25° C. |
| 1 | 2 | 4 | 6 | 9 | 12 |
| 2 | 4 | 6 | 9 | 15 | 18 |
| 5 | 8 | 14 | 21 | 30 | 37 |
| 10 | 15 | 21 | 34 | 48 | 61 |
| 15 | 19 | 32 | 47 | 64 | 75 |
| 30 | 30 | 48 | 70 | 90 | 98 |

EXAMPLE 5

Orange Juice Taste Test

In order to determine if the product of Example 1 is an effective generator and if it imparts any taste of its own upon flavors in which it is used, the following sample is tasted "blind" by a panel of flavorists:

| | Part by Weight |
|---|---|
| Potassium 2-[(1'-ethoxy)ethoxy]propanoate | 0.023 g |
| Orange Juice, reconstituted | 1.000 g |

When the orange juice is used as the control, the panel unanimously picks the sample containing the product of Example 1 as having "fresh squeezed orange juice flavor". The flavor is considered "clean" and has no "off-notes".

Other features, advantages and specific embodiments of this invention will become readily apparent to those exercising ordinary skill in the art after reading the foregoing disclosures. In this regard, while specific embodiments of this invention have been described in considerable detail, variations and modifications of these embodiments can be effected without departing from the spirit and scope of the invention as disclosed and claimed.

What is claimed is:

1. A compound of the general formula:

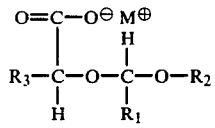

where $R_1$ is an alkyl having from 1 to 14 carbons, alkenyl having from 2 to 14 carbons, cycloalkyl, cycloalkenyl, aryl, or furyl having from 4 to 14 carbons; $R_2$ is alkyl, alkenyl, alkynyl, cycloalkyl, cycloalkenyl, or cycloalkynyl of from 1 to 7 carbons, aryl or oxyaryl of from 5 to 18 carbons, or a cycloaliphatic ether of from 5 to 6 carbons; and $R_3$ is hydrogen, alkyl, alkenyl, alkynyl, cycloalkyl, cycloalkenyl, or cycloalkynyl of from 1 to 7 carbons, aryl, or oxyaryl of from 5 to 18 carbons, or a cycloaliphatic ether of from 5 to 6 carbons, or a radical of the general formula:

where $R_4$ and $R_5$ independently are hydrogen or alkyl of from 1 to 6 carbons; and $R_6$ is aryl, alkylaryl, aryloxy, alkoxy, cyclic acetal of from 3 to 7 carbons, dioxyalkyenyl ether of from 4 to 8 carbons; and M is consumable cation other than hydrogen ion.

2. The compound of claim 1 wherein said compound is potassium 2-[(1'-ethoxy)ethoxy]propanoate.

3. The compound of claim 1 wherein said compound is potassium 2-[(1'-ethoxy)propoxy]propanoate.

4. The compound of claim 1 wherein said compound is calcium 2-[(1'-ethoxy)ethoxy]propanoate.

5. The compound of claim 1 wherein $R_2$ is methyl, ethyl, propyl, t-butyl, phenyl or butenyl.

6. The compound of claim 1 wherein M is $Na^+$, $K^+$, $Ca^{+2}$, $Al^{+3}$, or $NH_4^+$.

7. The compound of claim 1 wherein $R_2$ is alkyl.

8. The compound of claim 1 wherein $R_2$ is alkenyl.

9. A compound of the general formula:

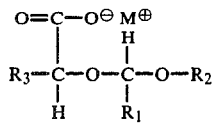

wherein $R_1$ is an alkyl having from 1 to 14 carbons, alkenyl having from 2 to 14 carbons, cycloalkyl, cycloalkenyl, aryl, or furyl having from 4 to 14 carbons; $R_2$ is alkyl of from 2 to 7 carbons, alkenyl, alkynyl, cycloalkyl, cycloalkenyl, or cycloalkynyl of from 1 to 7 carbons, aryl or oxyaryl of from 5 to 18 carbons, or a cycloaliphatic ether of from 5 to 6 carbons; and $R_3$ is hydrogen, alkyl, alkenyl, alkynyl, cycloalkyl, cycloalkenyl, or cycloalkynyl of from 1 to 7 carbons, aryl, or oxyaryl of from 5 to 18 carbons, or a cycloaliphatic ether of from 5 to 6 carbons, or a radical of the general formula:

where $R_4$ and $R_5$ independently are hydrogen or alkyl of from 1 to 6 carbons; and $R_6$ is aryl, alkylaryl, aryloxy, alkoxy, cyclic acetal of from 3 to 7 carbons, dioxyalkyenyl ether of from 4 to 8 carbons; and M is consumable cation is other than hydrogen ion.

10. The compound of claim 9 wherein M is $Na^+$, $K^+$, $Ca^{+2}$, $Al^{+3}$, or $NH_4^+$.

11. The compound of claim 9 wherein $R_2$ is alkenyl.

* * * * *

UNITED STATES PATENT AND TRADEMARK OFFICE
CERTIFICATE OF CORRECTION

PATENT NO. : 4,697,025
DATED : September 29, 1987
INVENTOR(S) : Brian Byrne

It is certified that error appears in the above-identified patent and that said Letters Patent is hereby corrected as shown below:

Column 2 - Line 52   " where R "

Should read:   -- where $R_1$ --

Column 3 - Lines 40 & 41   " (b) furyl;
    (i) an aliphatic "

Should read:   -- (b) furyl;
    R2 is
        (i) an aliphatic --

Signed and Sealed this

Twenty-second Day of March, 1988

Attest:

DONALD J. QUIGG

*Attesting Officer*    *Commissioner of Patents and Trademarks*